United States Patent [19]

Hayashi et al.

[11] 4,352,987
[45] Oct. 5, 1982

[54] STRUCTURE OF DENTAL X-RAY APPARATUS

[75] Inventors: Kazuo Hayashi; Mitsuhiko Hotta, both of Kyoto, Japan

[73] Assignee: Kabushiki Kaisha Morita Seisakusho, Kyoto, Japan

[21] Appl. No.: 124,532

[22] Filed: Feb. 25, 1980

Related U.S. Application Data

[63] Continuation of Ser. No. 864,538, Dec. 27, 1977, abandoned.

[51] Int. Cl.³ ............................................. G03B 41/16
[52] U.S. Cl. ..................................... 378/150; 378/38
[58] Field of Search ............... 250/511, 505, 512, 513

[56] References Cited

U.S. PATENT DOCUMENTS 3,536,913 10/1970 Huchel ........................... 250/439 P
3,849,649 11/1974 Carey .................................. 250/511

Primary Examiner—Craig E. Church
Attorney, Agent, or Firm—Koda and Androlia

[57] ABSTRACT

According to this invention, useless exposure of a human being to X-ray is avoided and X-ray film is economically used by providing the X-ray generator of a dental X-ray apparatus with an X-ray intercepting means by which the size of the opening or slit for X-ray beams flow is easily controlled. The X-ray apparatus comprises an X-ray generator, an X-ray film, an arm for supporting the X-ray generator and the X-ray film in such a manner that the X-ray generator faces the X-ray film. When the arm is rotated at a predetermined angle around the X-ray film thereby causing the X-ray generator to be rotated proportionally, the X-ray generator emits X-ray beams through the vertically elongated slit disposed in the X-ray generator's head.

1 Claim, 6 Drawing Figures

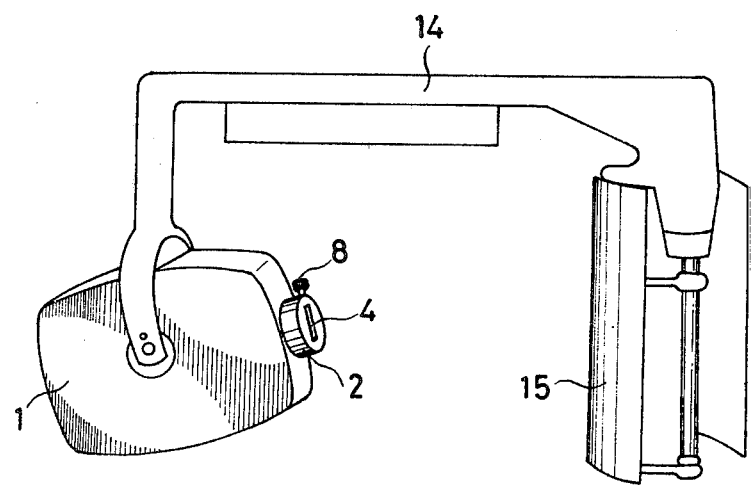
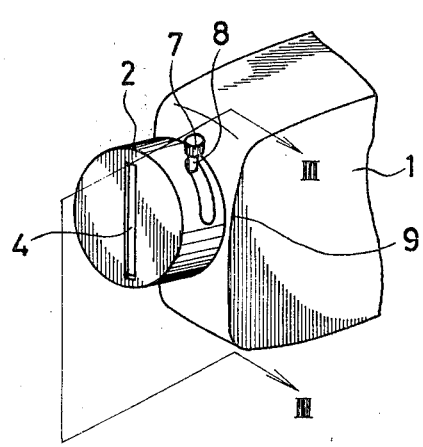
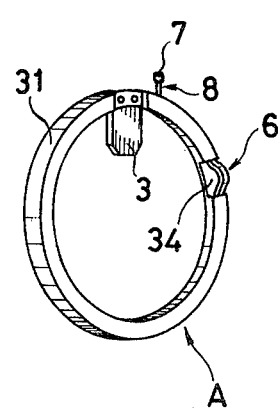

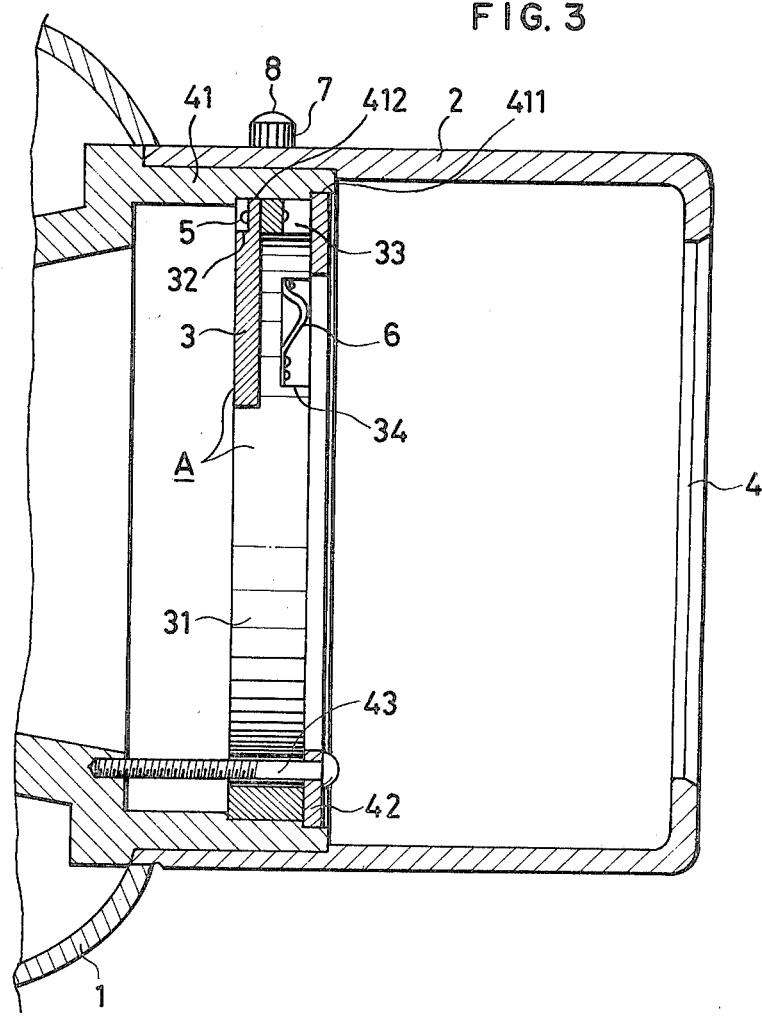

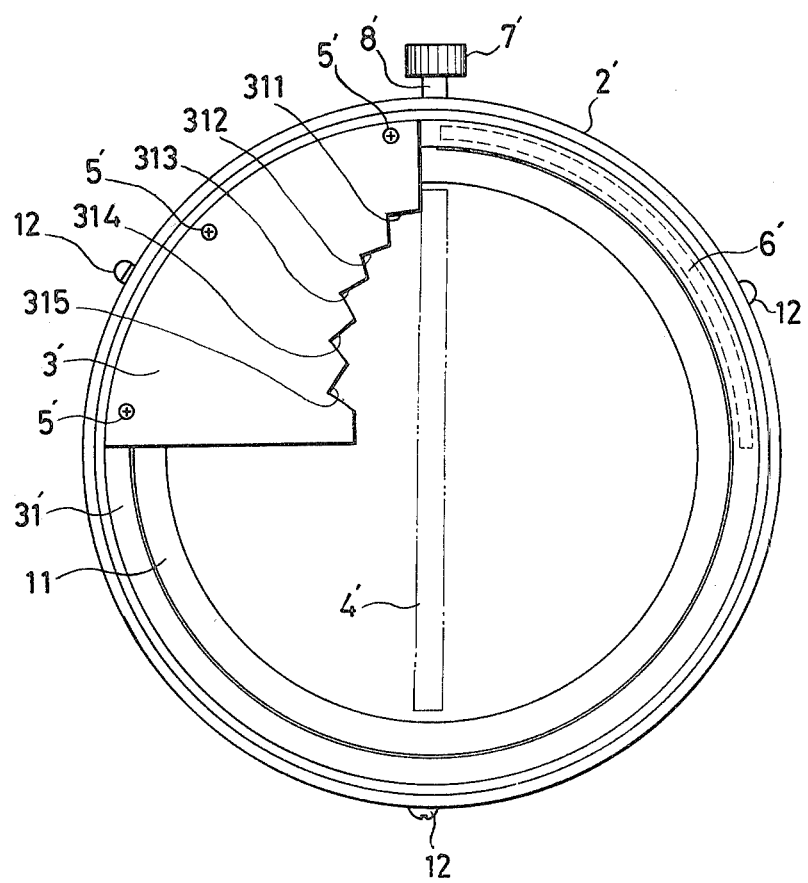

STRUCTURE OF DENTAL X-RAY APPARATUS

This is a continuation of application Ser. No. 864,538 filed Dec. 27, 1977 now abandoned.

BACKGROUND OF THE INVENTION

1. Field of the Invention

This invention relates to an X-ray generator of a dental X-ray apparatus used for taking continuous tomograms of the dental arch of a human being and, more particularly, to an X-ray generator in which the size of the slit for emitting X-ray beams therethrough can be controlled by sheltering either or both at the upper and the lower ends of the slit with intercepting means.

2. Prior Art

The X-ray generator with an X-ray tube therein of an X-ray apparatus which has so far been used for dental purposes includes a head in front whose front-wall is provided with a slit normally elongated in the vertical direction through which X-ray beams are emitted on the surface of the X-ray film. However, the X-ray emitting slit in the prior art generator has been equipped with no means for controlling the area on which the X-ray beams would be exposed.

Therefore, the following defects should be pointed out in the prior art generator. Namely, as well known, there are two kinds of photograhic regions in taking a tomogram of the dental arch of a human being; one of which is a wide region including the head, the nose besides the dental arch, while the other of which is a narrow one covering only the dental arch. On the other hand, an X-ray film for the apparatus is commercially obtainable for each purpose respectively. Nevertheless, it has been the general practice that one X-ray generator is used for these two purposes by using the same X-ray emitting slit vertically longer sized since the wide region contains the narrow region therein. In this way, however, even in the case where only the narrow region is required, the patient is forced to be exposed to X-rays to an unnecessarily wide extent, which may result in excessive exposure of X-rays to the patient and also unnecessary consumption of the film.

Thus, in making tomograms of the dental arch, a practical solution for adjusting the vertical size of X-ray emitting slit has been strongly longed for so that only the diseased part of the patient can be exposed to X-ray without changing the generator.

SUMMARY OF THE INVENTION

It is, therefore, a primary object of this invention to provide a structure of an X-ray apparatus for adjusting the height of the slit for emitting the X-ray beams for at least two types of exposures from the wide region to the narrow region. The present invention relates to an X-ray generator for X-raying the entire jaw for dental purposes including a screening plate at a cylindrical section of the generator, the screening plate being able to freely rotate along the peripheral direction of the cylindrical section, the screening plate further covering at least one end of a longitudinally narrow radiation emitting slit provided at a front part of the cylindrical section in such a way that a front edge of the screening plate crosses the radiation emitting slit nearly perpendicularly whereby the amount of X-ray radiation is appropriately adjustable depending upon the size and shape of the object to be photographed.

More particularly, the intercepting means comprises a ring which is equipped within the head so as to be rotated and stopped in the circumferential direction of the head, an X-ray intercepting plate projected in the centripetal direction from the ring, a manual level connected with the ring and projected from the head, a groove guide member for moving the manual lever therein which is cut through the cylindrical wall of the head, and a spring member for resiliently supporting the ring in the axial direction of the head so as to smoothly carry out the rotation and stopping.

In a preferable embodiment, the X-ray intercepting plate is arranged to be of a vertically longer rectangular plate and when the plate is moved to the position where the plate shelters the X-ray emitting slit, the height of the slit can be reduced to the limit corresponding to the distal end of the plate.

In a more preferable embodiment, the intercepting plate is made of a sectorial plate whose edge facing the rotational direction is equipped with steps-like notches in succession. By fractionally rotating the sectorial plate with steps-like notches, X-ray beams can be intercepted to various degrees.

The invention may be carried into practice in various ways but certain specific embodiments as applied in the two examples above-mentioned will be described by way of example with reference to the accompanying diagrammatic drawings.

BRIEF DESCRIPTION OF THE DRAWINGS

FIG. 1 is a perspective view of a dental X-ray apparatus provided with an X-ray generator according to the invention.

FIG. 2 is a perspective view on an enlarged scale of the X-ray generator.

FIG. 3 is a sectional view on an enlarged scale of the III—III line of FIG. 2.

FIG. 4 is a perspective view of an X-ray intercepting means according to the invention.

FIG. 6 is a cross-sectional view of the VI—VI line of FIG. 5.

DETAILED DESCRIPTION OF THE INVENTION

Figure 5:
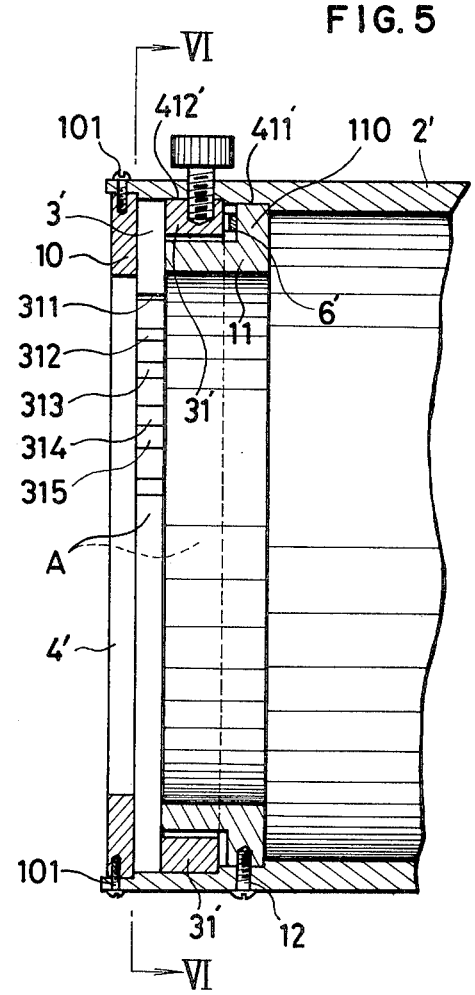
FIG. 5 is a longitudinal sectional view of another embodiment according to the invention.

In starting the explanation of the structure of an X-ray intercepting means according to the invention, the outline of a dental X-ray apparatus should be described with reference to FIG. 1. As in FIG. 1, an X-ray generator 1 and an X-ray film 15 are supported with an arm 14 thereby the head of the generator 1 facing the film 15. X-ray beams are emitted from the X-ray generator 1 through a vertically longer X-ray emitting slit 4 of a head 2 of a generator 1 to the surface of the film 15, while the arm 14 is moved along a predetermined angle close to the dental arch of a human being. In this way, a tomogram is taken of the dental arch of a human being.

The structure of an X-ray intercepting means according to the invention will be described hereinaftfer. As in FIGS. 1 through 6, an X-ray intercepting means A according to the invention comprises a ring 31 which is equipped within the head 2 of the X-ray generator 1 and is rotated and stopped in the circumferential direction of the head 2, an intercepting plate 3 projected in the centripetal direction from the ring 31, a manual lever 8 which is connected with the ring 31 and is projected from the head 2, a groove guide member 9 which is cut through the cylindrical wall of the head 2 so as to move the lever 8 to a preferable position, and a spring member for resiliently supporting the ring 31 in the axial direction of the head 2 so as to smoothly carry out the rotation and stopping of the ring 31.

The specific embodiment drawn in FIGS. 1 and 2 shows an embodiment where one vertically longer rectangular plate made of an X-ray impermeable material such as lead alloy castings or the like is used as the intercepting plate 3. The intercepting plate 3 projected in the centripetal direction from the ring 31 is connected to the back side of the ring 31 with a screw 5 in a scraped part 32 and a scraped part 33 corresponding to the part 32 is provided in front of the ring 31 to accomodate the leg of the screw 5. The manual lever 8 is screwed in the ring 31. In an inner wall of the ring 31 is formed an arched recess 34, to which a spring 6 (such as a leaf spring) waved in the axial direction of the head 2 is fixed with the top of the spring 6 slightly projecting ahead from the front surface of the ring 31. In order to equip the manufactured head 2 having the X-ray emitting slit 4 provided on the front wall of the head with the X-ray intercepting means according to the invention therein, it is necessary that, as in FIG. 3, within the head 2 is equipped a cylindrical body 41 concentric to the head whose inner wall has two cylindrical recesses 411 and 412 and that, as in FIG. 2, the guide groove 9 is cut through the cylindrical wall of the head 2 to move the manual lever 8 along the groove. The ring 31 having the intercepting plate 3 on the back is inserted in the recess 412. A fixing ring 42 is inserted in the recess 411 so that the top of the spring 6 is compressed slightly by the ring 42. The ring 42 is attached to the cylindrical body 41 with a long screw 43 in places in the circumferential direction of the ring 42. The manual lever 8 which is equipped with a knob 7 on its head is projected from the head 2 through the guide groove 9, as above 9, as abovementioned. When the lever 8 is shifted from one end, which is drawn in FIG. 2, to the other end of the guide groove 9, the upper end of the X-ray emitting slit 4 is sheltered with the intercepting plate 3. By the resilient force of the spring 6, the ring 31 is steadily sustained in the axial direction of the head 2. If the ring 31 is forcedly rotated by a force greater than the frictional force of the ring 31 by the spring 6 via the manual lever 8, the ring 31 is rotated in the circumferential direction of the head 2 and stops in a preferable position with the removal of the force. In an preferable embodiment drawn in FIG. 1 through 4, as the intercepting plate 3 is used one vertically longer rectangular plate which shelters the upper end of the emitting slit 4 inside the head.

In another preferable embodiment drawn in FIGS. 3 and 4, an intercepting plate is designed so that the plate can shelter an emitting slit to various degrees. That is to say an intercepting plate 3' in this embodiment is made of a sector whose center angle is approximately the right angle and whose edge (drawn vertically in FIG. 6) is equipped with several steps-like notches 311, 312, 313, 314 and 315. The intercepting plate 3' is attached to a ring 31' with a screw 5' (in places). The explanation of a manual lever 8' and a guide groove (not drawn in FIG. 6) is omitted as it is the same with the former embodiment. This embodiment differs from the former embodiment in the shape of the intercepting plate 3', in the position where the ring 31' is equipped within a head 2' (i.e., the position nearest to the back of the front wall of the head 2'), in the manner of a spring 6' and in the structure for supporting the ring 31'. That is, the ring 31' is equipped within the head 2' in contact with the inner wall of a front plate 10 (but more preferable if a small gap is between the ring 31' and the plate 10). More specifically, as in FIGS. 5 and 6, the ring 31' is inserted in a cylindrical recess 412' so that the intercepting plate 3' can be in contact with the inner wall of the front plate 10 while at the back of the ring 31' an inverted L-shaped (cross-sectionally) seat ring 11 is inserted in a cylindrical recess 411' and connected to the head 2' with a screw 12. Between the back of the ring 31' and a wall 110 of the seat ring 11 is pressedly put a leaf spring 6' which is waved in the axial direction of the head 2' and is in length approximately a quarter of the circumference of the head 2' (as in FIG. 6). The front plate 10 is connected with a screw 101. According to the structure above-mentioned, by rotating the ring 31' step by step via the manual lever 8', the sectional intercepting plate 3' shelters the emitting slit 4' with its steps-like notches 311, 312, 313, 314, and 315 so that the slit 4' is fractionally shortened. As compared with the former embodiment, therefore, this embodiment brings about such an advantage that the height of X-ray beams can be reduced to various degrees.

As shown in the embodiments above-mentioned, the X-ray generator according to the invention is equipped within its head with a ring which is rotated and stopped in the circumferential direction of the head, so that by moving the manual lever of the ring from outside the head, ready interception of X-ray beams can be obtained to various degrees with an X-ray intercepting plate projected in the centripetal direction from the ring sheltering any of the upper and lower ends of the slit. In particular, the intercepting plate 3 shelters or covers the radiation emitting slit 4 in such a way that the front edge of the intercepting plate 3 will cross the radiation emitting slit 4 substantially perpendicularly. The same sheltering can also be obtained at both ends of the slit as will be understood by the later explanation. Therefore, unnecessary exposure of a human being to X-ray is avoided and X-ray film is economically used, according to the invention.

While the invention has been particularly shown and described with reference to the preferred embodiments thereof, it will be understood by those ordinarily skilled in the art that the foregoing and other changes in form and detail may be made therein without departing from the spirit and scope of the invention. For example, the followings lie in the spirit and scope of the invention:

1. The simultaneous sheltering of both the upper and lower ends of an X-ray emitting slit by means of two intercepting plates forming a pair in a diametral direction of a ring.

2. The selected sheltering of the upper end or the lower end of an emitting slit by means of two independent intercepting-plates which are moved independently.

3. The employment of a seat ring rotatable by force instead of a fixed seat ring in the second embodiment thereby, fulfilling the purpose described in 2.

4. The change in shape of an intercepting plate and the alteration of the position where an intercepting plate is set.

5. The arrangement of the invented X-ray intercepting means in a preferable position inside the head of an X-ray generator.

6. The substitution, addition or alteration lying in the spirit and scope of the appended claims.

We claim:

1. An X-ray generator for X-raying an entire jaw for dental purposes including an X-ray source and a vertical X-ray emitting slit comprising a screening plate provided adjacent said X-ray emitting slit, said screening plate being rotatable relative to said slit, said screening plate covering at least one end of said radiation emitting slit, said screening plate further comprising:

a fan-shaped plate spanning substantially 90°; and
a plurality of notch steps provided on an edge of said fan-shaped plate which intercepts said emitting slit, each of said steps being arranged and configured to intercept said emitting plate substantially perpendicularly when said screening plate is rotated;
whereby a vertical height of said emitting slit can be adjusted.

* * * * *